United States Patent

Zamanian et al.

(10) Patent No.: US 7,493,800 B2
(45) Date of Patent: Feb. 24, 2009

(54) SAMPLING METHOD

(75) Inventors: Ahmad Zamanian, Victoria, TX (US);
Lawrence W. Dvorak, Port Lavaca, TX (US); Brian K. Reed, Victoria, TX (US)

(73) Assignee: Equistar Chemicals, LP, Houston, TX (US)

( * ) Notice: Subject to any disclaimer, the term of this patent is extended or adjusted under 35 U.S.C. 154(b) by 40 days.

(21) Appl. No.: 11/823,188

(22) Filed: Jun. 27, 2007

(65) Prior Publication Data

US 2009/0000359 A1    Jan. 1, 2009

(51) Int. Cl.
*G01N 1/00* (2006.01)
*B01D 35/00* (2006.01)

(52) U.S. Cl. .................... 73/61.59; 210/85
(58) Field of Classification Search ................. 73/61.41, 73/61.43, 61.44, 61.59; 137/2; 210/85
See application file for complete search history.

(56) References Cited

U.S. PATENT DOCUMENTS

| | | | | |
|---|---|---|---|---|
| 2,812,773 A | * | 11/1957 | McGee | ............ 137/487.5 |
| 3,220,930 A | * | 11/1965 | Thompson | ............ 196/46 |
| 3,359,787 A | * | 12/1967 | Zemanek, Jr. | ............ 73/61.49 |
| 3,515,988 A | * | 6/1970 | Shawhan | ............ 324/666 |
| 3,693,435 A | * | 9/1972 | Cox et al. | ............ 73/861.04 |
| 3,932,111 A | * | 1/1976 | Liknes et al. | ............ 431/202 |
| 5,070,725 A | * | 12/1991 | Cox et al. | ............ 73/61.44 |
| 5,090,238 A | * | 2/1992 | Jones | ............ 73/152.42 |
| 5,139,653 A | * | 8/1992 | Ludlam et al. | ............ 210/85 |
| 5,260,667 A | * | 11/1993 | Garcia-Golding et al. | ... 324/694 |
| 5,545,799 A | * | 8/1996 | Ritter | ............ 588/316 |
| 5,612,490 A | * | 3/1997 | Carlson et al. | ............ 73/61.43 |
| 7,351,779 B2 | * | 4/2008 | Iaccino et al. | ............ 526/206 |
| 2003/0106694 A1 | * | 6/2003 | Wiseman | ............ 166/379 |
| 2006/0053869 A1 | * | 3/2006 | Gysling et al. | ............ 73/61.44 |

\* cited by examiner

*Primary Examiner*—John Fitzgerald
(74) *Attorney, Agent, or Firm*—Roderick W. MacDonald

(57) ABSTRACT

A method for sampling a host liquid in a vessel to detect the presence of an undesired liquid in the host liquid and removing host liquid that contains undesired liquid from the vessel, wherein an electrical capacitance probe is employed to detect the presence of the undesired liquid, and the liquid that is passed by the capacitance probe is fed to an incinerator.

7 Claims, 2 Drawing Sheets

SAMPLING METHOD

BACKGROUND OF THE INVENTION

1. Field of the Invention

This invention relates to a method for analyzing a sample of a host liquid held in a vessel for the presence of an undesired liquid, and, if necessary, removing sufficient of the liquid in the vessel to remove the undesired liquid from that vessel.

2. Description of the Prior Art

Although, for sake of clarity and brevity, this invention is described in terms of an ethylene polymerization plant that produces a polyethylene product, this invention is broader in its application than polyethylene production plants.

Ethylene is polymerized to polyethylene homopolymers and co-polymers by a number of different processes to make different polymeric products such as low density polyethylene, high density polyethylene, and linear low density polyethylene which exhibits favorable characteristics found in both low density and high density polyethylenes. For sake of example only, this invention is described herein primarily in terms of a solution phase (solution) polymerization process for making high density polyethylene (HDPE).

Although originally used to make HDPE, the solution polymerization process has been adapted to copolymerization and the making of linear low density polyethylene. The system operates at lower pressures, from about 2000 to about 3000 psig, rather than the earlier high pressure, 50,000 psig, bulk or high-pressure polymerization process, and runs at temperatures of from about 300 to about 550 degrees Fahrenheit (F) using conventional Ziegler-Natta catalyst systems.

In the solution process a hydrocarbon such as n-hexane or cyclohexane, for example, is employed as the host medium (solvent) in which the polymerization reaction takes place. This host liquid solvent keeps the ethylene monomer, catalyst, and the polyethylene product in a fluid state, and also keeps these materials in intimate contact with one another to facilitate the polymerization reaction. The solvent also absorbs much of the exothermic heat from the polymerization reaction, and helps control the rate of ethylene consumption in the reaction.

The ethylene resides in the polymerization reactor for a few minutes, and, as it polymerizes, remains dissolved in the host solvent.

Downstream, the polyethylene is processed for the removal of catalyst followed by solvent separation and recovery for re-use in the reactor. The remaining molten polyethylene is fed to a drying, extruding, and pelletizing system wherein it is converted to solid polyethylene pellets. The pellets are then packaged and marketed as a product of the polyethylene production plant.

The solvent is thoroughly dried of its water content because water, being polar, acts as a poison to the Ziegler-Natta catalyst system. Only a trace of water in the solvent can adversely affect the catalyst. These catalyst systems employ, for example, titanium tetrachloride/trialkyl aluminum or other transition metals such as zirconium and vanadium in place of the titanium. These catalyst systems are well known in the art and more detail is not necessary to inform one skilled in the art.

Heretofore, to determine if water was present in a tank holding a supply solvent, a sample was hand drained by an operator into a clear container, and then visually inspected for the presence of water that naturally separates out from the hydrocarbonaceous solvent. This sample was then passed to a sump that was exposed to the ambient atmosphere. If water was observed by the operator to be present in the sample, solvent was drained from the tank into the atmospherically exposed sump for a period of time. Then another sample was taken by hand and visually inspected for the presence of water. These steps were repeated until no water was seen in the hand sample taken by the operator. This process could require the taking of a number of samples before all the undesired water was removed from the solvent holding tank.

This hand sampling process sometimes led to the removal to the open air sump of more solvent than necessary to remove the undesired water because the operator could drain solvent that did not contain water into the sump before he took his next hand sample. In other words, the operator had no effective, much less accurate, way of determining whether all the water had been removed except by trial and error hand sampling, and this could cause the removal of solvent that was not contaminated with water. This sampling process could, therefore, cause a lot of the solvent, a volatile hydrocarbon material, to be passed into the sump that was exposed to the ambient atmosphere, thereby allowing the solvent to vaporize and enter the atmosphere. Thus, a laborious hand sampling procedure was heretofore employed that not only could waste dry solvent, but delivered to the ambient atmosphere more solvent than necessary or desirable.

Accordingly, it is desirable to be able accurately to detect the presence of even minute amounts of water in as small a volume of solvent sample as possible before that solvent is employed in the polymerization process. It is equally desirable to be able to take a minimum number of samples of solvent, each sample in a minimum volume, during the sampling of that host liquid.

It is just as desirable that any additional solvent that is drained to remove water from the holding tank, is taken from the tank in a manner such that only the minimum amount of solvent is taken that is necessary to remove the water, and that minimum amount of solvent is disposed of in an environmentally friendly way.

This invention accomplishes all of the foregoing.

SUMMARY OF THE INVENTION

In accordance with this invention, there is provided a method for detecting the presence of an undesired liquid or liquids in a host liquid in a holding vessel by providing at least one electrical capacitance probe in fluid communication with the vessel, the probe having a set point for essentially pure host liquid, draining a sample of liquid from the vessel, and sensing from the sample by way of the probe whether undesired liquid is present in the sample. If undesired liquid is present in the sample, liquid is drained from the vessel until the probe indicates essentially pure host liquid is present in the drained liquid. The sample taken and any liquid that is drained to remove undesirable liquid are passed to a combustor to incinerate same.

DETAILED DESCRIPTION OF THE INVENTION

Figure 1:
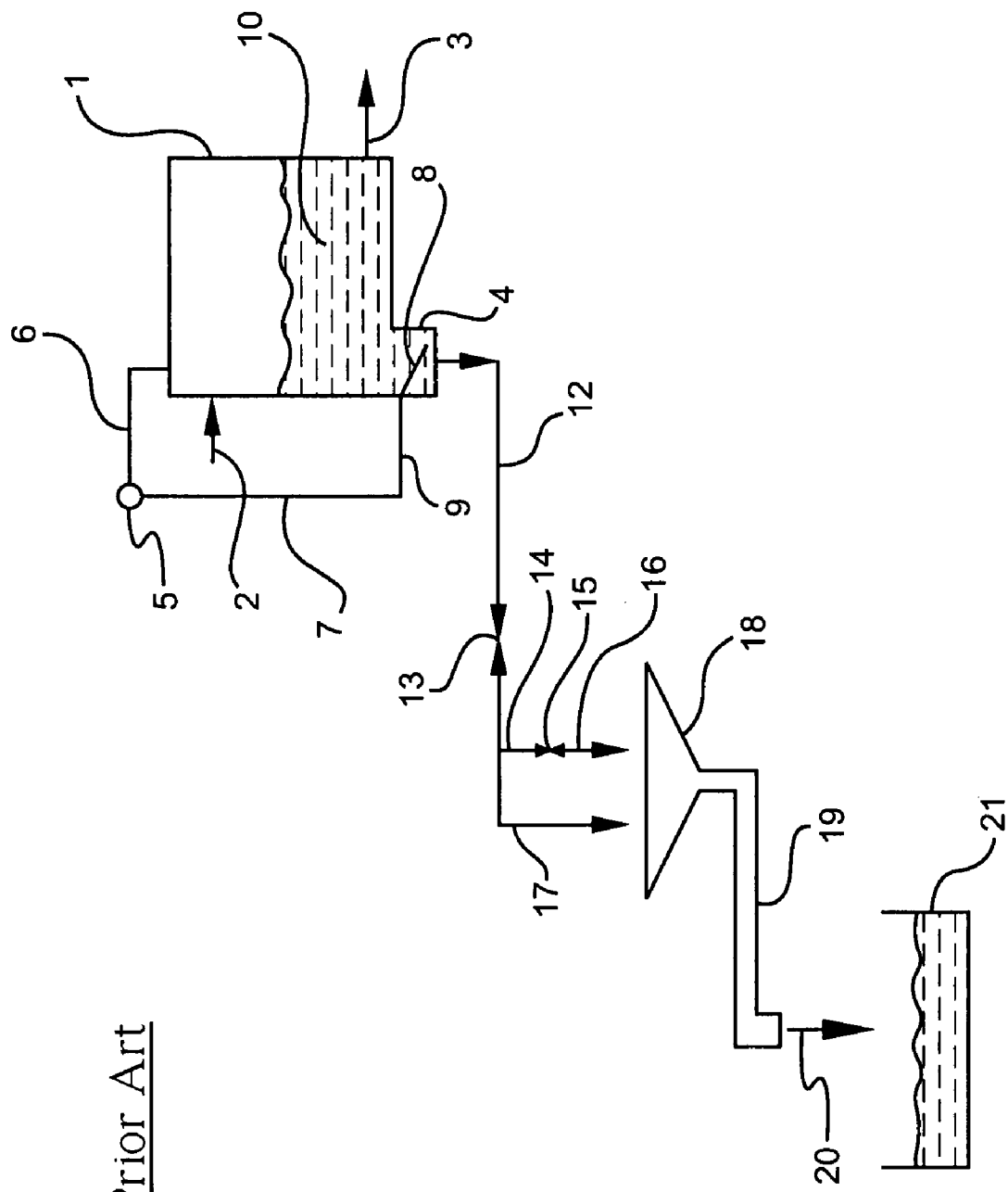
FIG. 1 shows a flow diagram for the prior art sampling process described hereinabove.

FIG. 1 shows a solvent holding (surge) tank 1 typically used in a polyethylene production plant (not shown) which receives and temporarily holds a body of solvent 10 that is to be employed in the polymerization process. Tank 1 can be used to hold newly received solvent, solvent recycled from the polymerization plant, or both. It is essential for the operating life of the catalyst used in the polymerization process that the solvent in tank 1 be as free as possible of catalyst poisons such as water.

To this end, even though the solvent introduced into tank 1 by way of conduit 2 has already been dried, a sump 4 is provided in a lower portion of tank 1 wherein water can and will collect due to the density difference between it and the solvent. This sump is provided due to the possibility of the formation of water condensate in the solvent during its transport, processing, and the like.

Solvent is removed from tank 1 by way of conduit 3 for use in the polymerization process. During the operation of the plant and of this invention, tank 1 can be in the state of being initially filled with solvent, having additional solvent added by way of line 2, and/or having solvent removed from tank 1 by way of line 3, any or all of which conditions can cause turbulence in the body of solvent 10 inside tank 1 and in the liquid inside sump 4.

The prior art detection device was a standard, commercially available pressure differential system which included a Rosemont meter 5. Meter 5 was calibrated for pure solvent so that when water was present in sump 4 the pressure differential increased thereby indicating that water needed to be drained from that sump.

The pressure differential system included, besides meter 5, a low pressure line (leg) 6 in fluid communication with the interior of tank 1 and a high pressure leg 7-9 that communicated with a dip tube 8 that was disposed inside sump 4. More about this in FIG. 2. Turbulence in solvent body 10, including sump 4, caused this pressure differential system to give inaccurate indications of the presence of water in sump 4.

When meter 5 did indicate water presence in the manner aforesaid, an operator had physically to go to the location of drain pipe 12 and its drain valve 13 to open valve 13 and let liquid from sump 4 drain by way of conduit 17, funnel 18, and conduit 19 into open air (atmospheric) sump 21 as shown by arrow 20. The operator then had to turn to the location of sampling tubing 14 and sampling valve 15 to open valve 15 and take a physical sample of sump 4 liquid by holding a clear receptacle under tubing 16 to catch the sample. Thereafter valve 13 was closed. During this procedure a lot of solvent flowed into sump 21. The operator then visually inspected the sample to see if water was actually present. If water was not present due to the inaccuracy of meter 5, the sample was poured into funnel 18 and passed through conduit 19 into sump 21. The liquid drained from sump 4 plus the sample resided in sump 21 until the solvent evaporated into the ambient atmosphere.

If the sample indicated the presence of water, valve 13 was opened to allow an arbitrary volume of liquid 10 to drain by way of lines 17 and 19 into sump 21 after which another sample was taken by the operator from line 16 for visual inspection to see if all the water had been removed from sump 4. If water was seen in this second sample, the procedure of draining for an arbitrary period of time followed by another hand sample was repeated until a sample was obtained that showed no water. This was a hit or miss procedure in that water free solvent could be drained from the sump before the operator took his next sample. Thus, unnecessary amounts of solvent were sent to sump 21 before a water free sample was found, and unnecessary amounts of solvent were sent to sump 21 to be allowed to evaporate into the atmosphere.

This was a laborious process that was unpopular with the operators, wasteful of operator time, inaccurate in that it often required the taking of a large number of samples, and often wasteful of water free solvent. It was also an environmentally unfriendly process in that organic solvent was allowed to evaporate into the ambient atmosphere of the plant.

Figure 2:
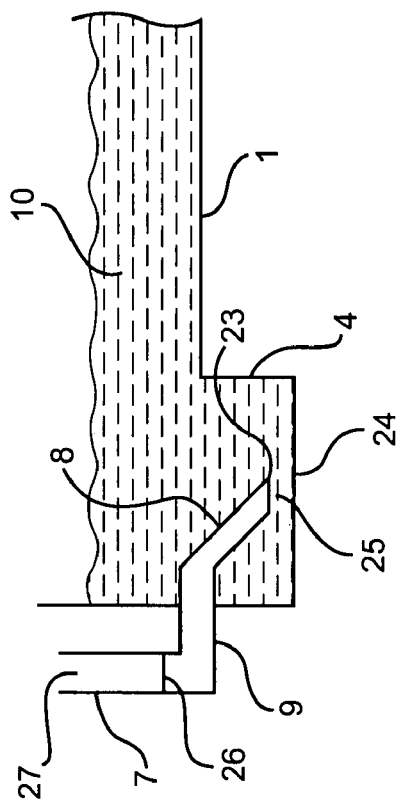
FIG. 2 shows an enlarged view of part of the apparatus of FIG. 1.

FIG. 2 shows an enlargement of sump 4 of FIG. 1. FIG. 2 shows that dip tube 8 extends close to the bottom 24 of sump 4, typically about 1 inch above bottom 24. This Figure also shows that dip tube 8 and portion 9 of the high pressure leg is filled with liquid 10. Nitrogen is imposed above the upper level 26 of liquid 10 inside of portion 7 of the high pressure leg to fill the high pressure leg from liquid level 26 up to meter 5 (FIG. 1). A nitrogen blanket is maintained inside tank 1 above the top of solvent body 10 so that low pressure leg 6 is also filled with nitrogen. The nitrogen in tank 1, low pressure leg 6, and high pressure leg portion 7 is from a common nitrogen supply source so that the nitrogen pressure in tank 1, line 6, and line 7 is essentially the same. This maintains essentially no pressure differential across meter 5 unless and until water collects in the bottom of sump 4

Figure 3:
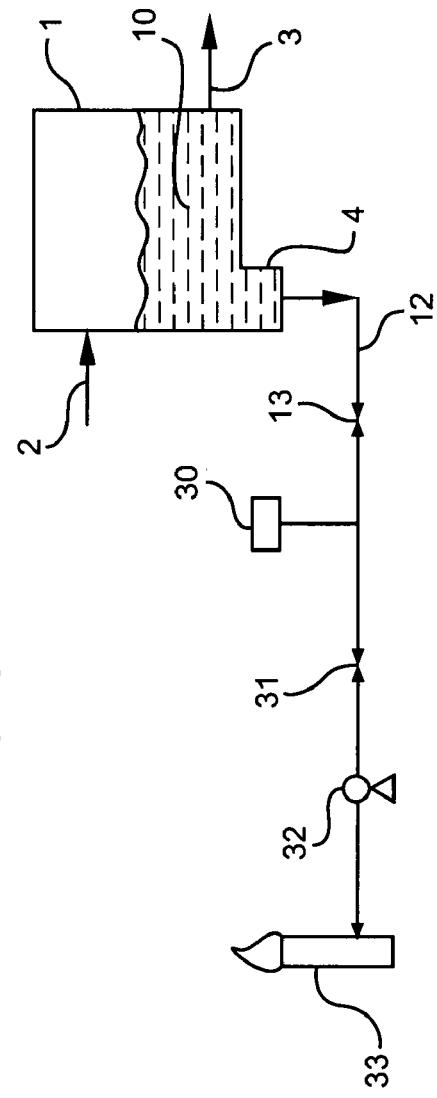
FIG. 3 shows one embodiment of a sampling process within this invention.

FIG. 3 shows tank 1 with the same sump 4, drain line 12, and drain valve 13, but modified to carry out a process of this invention. Line 12 carries an electrical capacitance probe (conductivity probe) 30 that is in fluid communication with the interior of line 12, a second drain valve 31, and a liquid pump 32. Line 12 is also in fluid communication with a combustor 33 for incinerating liquid removed from sump 4 during the sampling and, if required, draining process until water free solvent is obtained from the bottom of sump 4. The incinerator 33 shown in FIG. 3 is a standard flare that is present in essentially all petrochemical plants.

In operation, initially line 12 is empty of liquid downstream of valve 13, and valves 13 and 31 are closed. The operator opens valve 13, with valve 31 cracked to allow vapor to escape, to allow liquid 10 to fill line 12 downstream of valve 13 and upstream of a now closed valve 31. This puts probe 30 into fluid communication with liquid 10. Probe 10 can be a commercially available capacitance probe such as the Sitrans LC 300 available from Siemens Militronics Process Instruments, Inc.

The set point for probe 10 is calibrated for essentially pure solvent 10 so that the presence of any water in liquid 10 in pipe 12 downstream of valve 13 will give a reading different from that set point, and thereby indicate the presence of water in an accurate manner that is not affected in any manner by turbulence in the body of liquid 10 that resides in tank 1 and sump 4. This is so whether tank 1 is initially being filled with solvent by way of line 2, having solvent added to an already partially filled tank by way of line 2, and/or having solvent removed by way of line 3a for use in the plant.

If probe 10 indicates that no water is present, valve 13 is kept closed and only liquid downstream of valve 13 is disposed of. This is done by opening valve 31 and pumping the liquid to flare 33 wherein it is incinerated. Thus, no organic solvent is allowed to evaporate, in kind, into the ambient air.

If probe 10 indicates the presence of water, valves 13 and 31 are opened to allow liquid continually to be drained in a controlled fashion to flare 33 until probe 10, which continually monitors the flow of liquid thereby, indicates that no water is present in the liquid with which probe 10 is in fluid communication. Valve 13 is then promptly closed so that only minimal water free solvent, between probe 10 and valve 13, is passed to flare 33. Probe 10 and valve 13 can be placed quite close to one another so that this minimal amount of water free solvent can be kept very small in volume.

It can be seen by the foregoing that the process of this invention is much less involved for the operator. The capacitance probe 10 is a more accurate instrument than the pressure differential system of FIG. 1, thereby reducing wasted solvent. In this invention, probe 10 is employed in a manner such that the number of samples taken, when water is present in sump 4, is reduced to one sample, and, at the same time, the amount of solvent drained before water free solvent is detected by probe 10 is greatly minimized. Further, the solvent that is taken as a sample and the solvent that is drained, if water is present, are disposed of in a more environmentally friendly manner.

We claim:

1. In a method for detecting the presence of at least one undesired liquid in a host liquid in a collection vessel for said host liquid, said vessel having in a lower part thereof at least one sump having an interior in fluid communication with said collection vessel, said at least one sump having at least one drain line that has an open interior in fluid communication with said at least one sump interior, the improvement comprising providing at least one electrical capacitance probe in communication with said at least one drain line interior, said probe having a set point for indicating essentially pure host liquid, employing a first valve in said at least one drain line upstream of and close to said probe, employing a second valve in said at least one drain line downstream of said probe, initially closing both said first and second valves so that said at least one drain line downstream of said first valve contains vapor and is empty of said host liquid, opening said first valve and cracking said second valve to remove said vapor from said at least one drain line downstream of said first valve until said host liquid is in communication with said probe and said host liquid fills said at least one drain line downstream of said first valve and upstream of said second valve at which time said second valve is closed, if no undesired liquid is detected by said probe keeping said first valve closed and opening said second valve, if undesired liquid is detected by said probe leaving said first and second valves open until no undesired liquid is detected by said probe at which time said first valve is closed, and passing said host liquid and any other of said liquid drained from said sump to a combustor to incinerate same, whereby a minimal amount of said host liquid that is free of said undesired liquid is passed to said combustor.

2. The method of claim 1 wherein said undesired liquid is at least water.

3. The method of claim 1 wherein said combustor is at least one incinerating flare.

4. The method of claim 1 wherein said host liquid is at least one hydrocarbon.

5. The method of claim 4 wherein said vessel is a holding tank in an ethylene polymerization plant that employs a hydrocarbon as the solvent in the ethylene polymerization step, said host liquid is said hydrocarbon solvent, said undesired liquid is water, and said combustor is a flare.

6. The method of claim 5 wherein said host liquid is at least one of n-hexane and cyclohexane.

7. The method of claim 5 wherein said ethylene polymerization plant employs a solution phase polymerizing process to produce high density polyethylene.

* * * * *